United States Patent [19]

Melsky et al.

[11] Patent Number: 5,575,770
[45] Date of Patent: Nov. 19, 1996

[54] IMPLANTABLE DRUG INFUSION SYSTEM WITH SAFE BOLUS CAPABILITY

[75] Inventors: Gerald S. Melsky, Lexington; Bradley J. Enegren, Norfolk, both of Mass.

[73] Assignee: Therex Corporation, Walpole, Mass.

[21] Appl. No.: 417,240

[22] Filed: Apr. 5, 1995

[51] Int. Cl.⁶ .................................................. A61M 11/00
[52] U.S. Cl. ............................ 604/93; 604/131; 604/132; 604/86
[58] Field of Search ................................. 604/86, 93, 131, 604/141, 891.1, 30, 132, 83–85, 236, 247, 151

[56] References Cited

U.S. PATENT DOCUMENTS

| | | | |
|---|---|---|---|
| 3,951,147 | 4/1976 | Tucker et al. | 604/891.1 |
| 4,193,397 | 3/1980 | Tucker et al. | |
| 4,496,343 | 1/1985 | Prosl et al. | |
| 4,668,231 | 5/1987 | de Vries et al. | 604/891.1 |
| 4,886,499 | 12/1989 | Cirelli et al. | 604/131 |
| 4,902,278 | 2/1990 | Maget et al. | 604/132 |
| 4,978,338 | 12/1990 | Melsky et al. | 604/93 |
| 5,395,324 | 3/1995 | Hinrichs et al. | 604/86 |
| 5,445,616 | 8/1995 | Kratoska et al. | 604/141 |

*Primary Examiner*—Randall L. Green
*Assistant Examiner*—V. Alexander
*Attorney, Agent, or Firm*—Cesari and McKenna

[57] ABSTRACT

An implantable infusion device includes a housing having opposite first and second walls and a relatively large blind passage extending into the housing from the first wall toward the second wall. A first self-sealing septum blocks the passage at the first wall and a second self-sealing septum blocks the passage at a location therein spaced from the first septum thereby defining an infusate chamber between the first and second septa and a blind chamber between the second septum and the housing second wall. A fluid pathway containing a normally closed valve extends from the infusate chamber to the exterior of the housing and a lever connected to the valve is located in the blind chamber. That lever may be depressed to open the valve only by a needle inserted through the two septa into the blind chamber which needle has a side opening aligned with the infusate chamber when such depression occurs.

12 Claims, 3 Drawing Sheets

IMPLANTABLE DRUG INFUSION SYSTEM WITH SAFE BOLUS CAPABILITY

FIELD OF THE INVENTION

This invention relates to an implantable drug infusion system. It relates more particularly to an implantable infusion pump which allows drugs to be bolused directly to the pump's outlet catheter.

BACKGROUND OF THE INVENTION

Implantable drug infusion pumps have been in existance for many years. They are used primarily for the long-term infusion of drugs in patients having chronic diseases such as diabetes, cancer and the like. In general, such pumps comprise a pressurized drug source which can be refilled while the device is implanted. A flow regulator regulates the flow of fluid from the source to an outlet catheter which delivers the drug from the flow regulator to a specific infusion site in the body; see, for example, U.S. Pat. No. 4,978,338 and the references cited therein.

Implantable pumps also exist which contain means whereby a drug or other fluid can be administered directly to the patient via the pump's outlet catheter, bypassing the pump's pressurized source; see for example, U.S. Pat. No. 4,496,343. Such a feature is considered essential in order to make the pump a versatile therapeutic tool. Indeed, there are many situations in which supplemental medication must be administered to a patient in addition to the drug being slowly infused into the patient from the pump's drug source. For example, fluids which are opaque to x-rays are sometimes injected through the pump's outlet catheter in order to verify that the pump is indeed infusing those organs or parts of the body which have been targeted for the prescribed drug therapy. As another example, if the pump's outlet catheter is positioned in a blood vessel, there is the potential that the catheter may become occluded by blood clots or thrombus. In such a situation, fluid flow through the catheter can be restored if an agent which can dissolve clots can be injected directly into the lumen of the outlet catheter.

FIG. 1 illustrates a typical prior pump with a bolus capability. It includes a housing 10 having an internal chamber 12 containing a collapsible fluid reservoir 14, e.g., a bellows capsule. Extending down into the top of housing 10 is an inlet port 16 which is connected to the interior of the reservoir 14 by an inlet conduit 18 in housing 10. The mouth of the inlet port 16 is closed by a self-sealing, needle-penetrable septum 20. The septum effectively isolates the port segment 16a below the septum, the conduit 18 and the interior of reservoir 14 from the atmosphere. The segment 16a thus forms a refill chamber in housing 10.

Also formed in housing 10 is an outlet passage 22 which leads from the interior of reservoir 14 to a fluid flow regulator 24, e.g., a capillary tube. The outlet from regulator 24 extends to one arm of a T-shaped outlet conduit 26 formed in housing 10, the leg of the T being connected to a flexible outlet catheter 28. When the pump is implanted, the distal end of catheter 28 is positioned at a selected infusion site in the body.

The other arm of outlet conduit 26 leads to a bolus inlet port 32 extending down into housing 10. The mouth of port 32 is closed by a self-sealing septum 34 similar to septum 20 thereby isolating the lower end segment 32a of passage 32 from the atmosphere. Thus that segment constitutes a bolus chamber in housing 10.

The chamber 12 of the pump is normally filled with a fluid such as triclorofluoromethane which vaporizes at physiological temperatures. Thus, when the pump is implanted in the body, the fluid in chamber 12 will vaporize and exert a positive pressure on reservoir 14 which tends to collapse the reservoir so that an infusate in the reservoir will be forced out of the reservoir through the outlet passage 22, regulator 24 and conduit 26 to the outlet catheter 28. Septum 34 prevents infusate in reservoir 14 from escaping through bolus port 32. As described in the above patents, infusate will continue to flow from reservoir 14 to the patient in a controlled manner until the contents of reservoir 14 are depleted.

The methods used to refill reservoir 14 or to bolus fluid directly to catheter 28 via the bolus chamber 32a are very similar. In general, a hollow needle is connected to a syringe containing the fluid to be injected. The needle is then inserted through the patient's skin above the implanted pump and through one of the septa 20 and 34 at the top of the pump. The fluid is injected through the needle and into the chamber 16a or 32a below the corresponding septum. The conduit 18 or 26 within the pump conducts the fluid either to the reservoir 14 or directly to catheter 28 depending upon which septum 20 or 34 has been penetrated.

Thus, if the needle penetrates septum 20 the delivered drug flows into reservoir 14. In that event, as described in the above patents, the refilling of the reservoir also exerts positive pressure on the fluid inside chamber 12 so that that fluid condenses thereby, in effect, recharging the pump. On the other hand, if the needle is inserted through septum 24, the delivered drug is bolused to outlet catheter 28, thereby bypassing reservoir 14 and flow regulator 24.

Normally, it is up to the healthcare professional to access the correct septum for the type of procedure to be performed, i.e., either reservoir refill or bolus to the outlet catheter. As might be expected, accidents have occurred in the past because the wrong septum was accessed inadvertently. For example, the drug which was intended to be injected into the pump's reservoir 14 to refill the reservoir was injected instead directly into the patient via the outlet catheter 28. Obviously such accidents can be dangerous to the patient. For example, in some cases, the reservoir 14 of a given pump may be filled with as much as a four week's supply of drug. Depending upon the drug used, such a four week's supply may be harmful if administered to the patient all at once by injection through the septum 34 instead of the septum 20. It would be desirable, therefore, if there existed an implantable pump having dual inlet ports which prevented such misdelivery of drugs to the pump.

SUMMARY OF THE INVENTION

Accordingly, the present invention aims to provide an improved implantable pump of the type having a bolus capability.

Another object of the invention is to provide an improved implantable dual chamber pump which prevents a healthcare professional from injecting a drug into the wrong chamber of the pump.

Still another object of the invention is to provide an implantable infusion pump with a bolus capability which is relatively easy to manufacture and to assemble.

A further object of the invention is to provide such a pump which is relatively inexpensive to make in quantity.

Other objects will, in part, be obvious and will, in part, appear hereinafter. The invention accordingly comprises the features of construction, combination of elements and arrangement of parts which will be exemplified in the following detailed description, and the scope of the invention will be in the claims.

Briefly, our infusion pump is somewhat similar to the conventional one depicted in FIG. 1 in that it includes a pumpable main infusate reservoir which can be refilled by injection through a self-sealing refill septum. The pump also includes a bolus septum which may be penetrated by a needle so that drugs can be bolused directly to the pump's outlet catheter.

The present pump differs from the prior ones, however, in that changes are made to the bolus chamber and to the fluid pathway between that chamber and the outlet catheter to prevent a drug intended to refill the pump's infusate reservoir from being bolused directly to the pump's outlet catheter and to prevent a bolus dose of infusate from being injected into the infusate reservoir.

As will be described in more detail later, the septum used to access the bolus pathway to the outlet catheter of our pump is replaced by a pair of septa spaced one on top of the other so that the bolus chamber is situated between those two septa. A passage exists between that chamber and the pump's outlet catheter which passage is normally closed by a valve. The valve may be opened by depressing a lever located in the housing below the stacked septa.

In order to perform a bolus injection, infusate must be introduced into the bolus chamber between the two stacked septa and the valve in the passage leading from that chamber to the outlet catheter must be opened by depressing the aforementioned lever. These two events can only occur by inserting a special needle through both of the stacked septa.

Unlike needles ordinarily used to access implanted pumps, this needle is closed at the tip and has a side opening spaced partway up the needle shaft form that tip. When the needle is fully inserted through both stacked septa, the opening in the needle shaft lines up with bolus chamber between the septa and the tip of the needle depresses the lever located below the septa thereby opening the safety valve. With the special bolus needle in place, a continuous flowpath is created from the hub of the needle to the pump's outlet catheter.

This type of pump is safer and more foolproof than infusion pumps with a bolus capability which lack such stacked septa and a safety valve. Since a special needle is used for the bolus procedure and for no other procedure, this needle may be clearly labeled with a warning that the needle is only to be used for an injection directly into the patient and that the needle is not to be used for refilling the pump's infusate reservoir.

If a refill needle, i.e., a standard needle with an open tip and no side opening, is inserted inadvertently into the bolus port during an attempted refill of the pump's reservoir, no fluid can be injected into the patient. This is because if the needle is inserted into the bolus port so that the opening at the needle tip is located in the bolus chamber, the safety valve in the outlet passage from that chamber would remain closed because the needle has not depressed the valve actuating lever. On the hand, if that ordinary needle is inserted through both septa in the bolus port sufficiently to depress the valve-actuating lever, the opening at the needle tip would not be aligned with the bolus chamber, i.e., it would be positioned below both of the stacked septa in the bolus port. Therefor, the fluid from the needle could not flow to the bolus chamber and thence to the outlet catheter. In other words, that ordinary refill needle cannot depress the lever which opens the safety valve and simultaneously inject fluid into the bolus chamber between the bolus septa; only the special bolus needle can do that.

By the same token, the special bolus needle cannot be used to refill the pump's infusate reservoir because the side opening in the shaft of the bolus needle would not empty into the pump's refill chamber if that needle should be inserted through the refill septum, i.e., the material of the refill septum would seal the side opening of the needle.

Thus, our pump and the special bolus needle associated therewith prevents the accidental misdelivery of a drug to the pump's two inlet ports. This safety feature may be incorporated relatively easily into otherwise more or less standard infusion pumps without adding materially to their costs. Our pump should, therefore, find wide acceptance wherever infusion pumps having a bolus capability are prescribed.

BRIEF DESCRIPTION OF THE DRAWINGS

For a fuller understanding of the nature and objects of the invention, reference should be had to the following detailed description taken in connection with the accompanying drawings, in which.

DESCRIPTION OF THE PREFERRED EMBODIMENT

Figure 1:
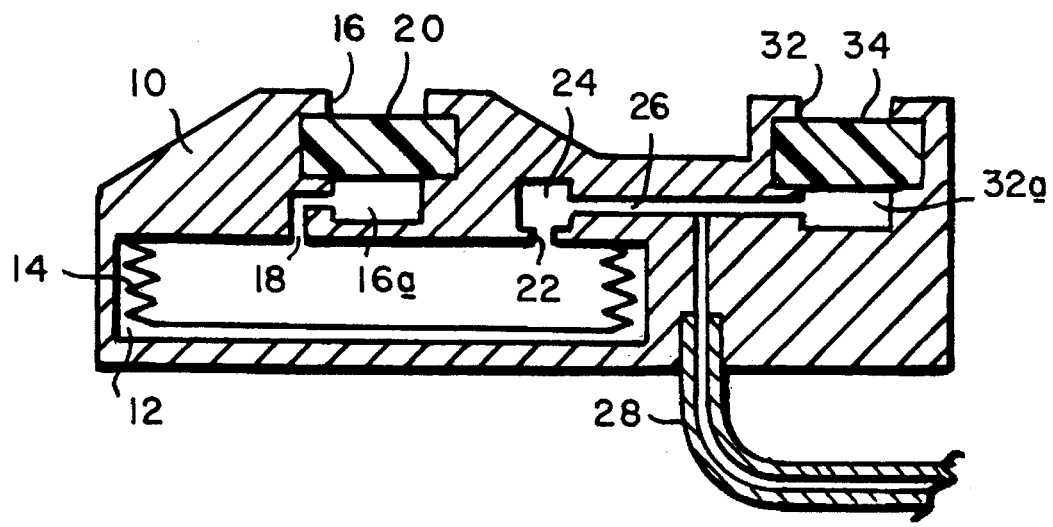
FIG. 1, already described, is a sectional view of a conventional implantable infusion pump having a bolus capability.
Figure 2:
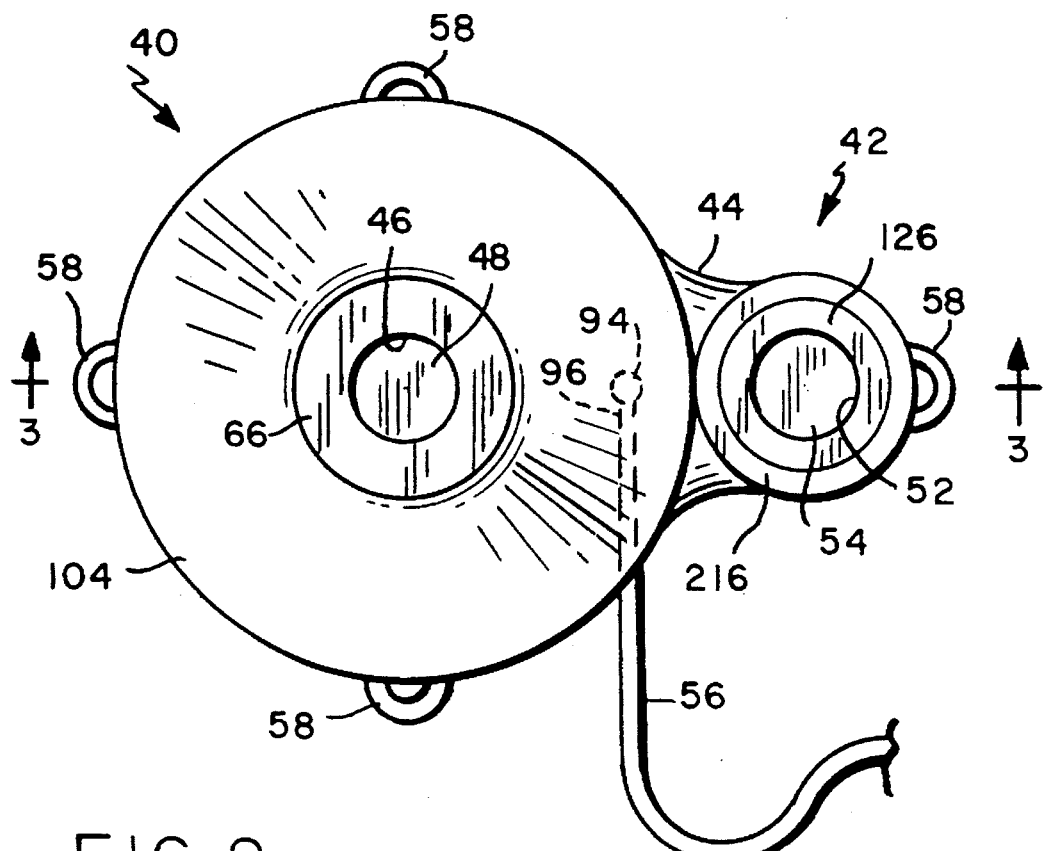
FIG. 2 is a plan view of an infusion pump with a safe bolus capability incorporating the invention.
Figure 3:
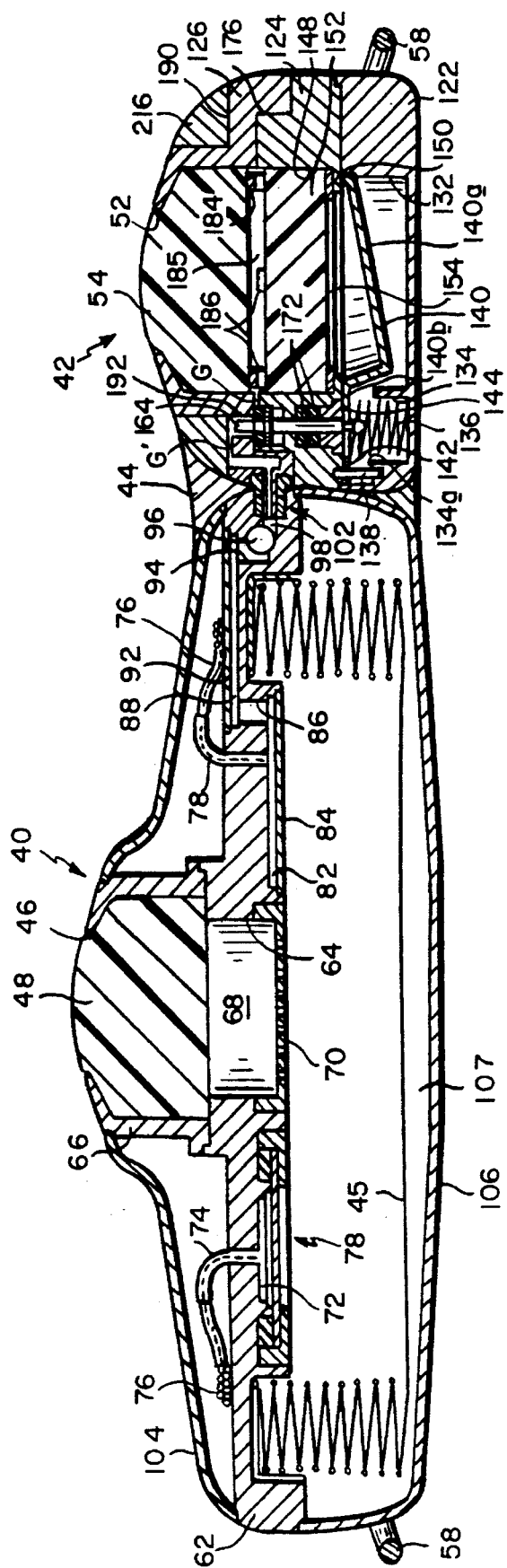
FIG. 3 is a sectional view on a larger scale taken along line 3—3 of FIG. 2 showing the pump's safety valve in its closed position.

Referring to FIGS. 2 and 3 of the drawings, our infusion pump comprises a generally cylindrical main body shown generally at 40 and a smaller, generally cylindrical bolus head shown generally at 42 connected by a neck 44 to body 40. Body 40 contains a pumpable infusate reservoir 45 (FIG. 3) which may be accessed from without through an inlet port 46 whose entrance is closed by a self-sealing rubber septum 48 present at the top surface of body 40. Bolus head 42 likewise includes an inlet port 52 at the top of the head which is closed by a self-sealing rubber septum 54. By inserting a hollow needle through the septum 48, reservoir 45 can be filled with infusate which may thereupon be pumped from reservoir 45 to a flexible outlet catheter 56 which extends from the pump at the neck 44. Also, by inserting a hollow needle through the bolus septum 54, a bolus dose of drug may be conducted from that needle directly to the outlet catheter 56.

A plurality of suture rings 58 are distributed around the perimeter of the pump so that when the pump is implanted in the body, those rings may be sutured to adjacent tissue to anchor the pump.

As best seen in FIG. 3, the pump body 40 comprises a rigid center plate 62 which supports the various elements of body 40. The infusate reservoir 45 is mounted to the underside of plate 62. In the illustrated pump embodiment, reservoir 45 is a metal bellows capsule having an open end secured to the underside of the plate as disclosed, for example, in U.S. Pat. No. 4,978,338, the opposite end of the capsule being closed.

Plate 62 has a relatively large diameter central opening 64 extending through plate 62 to the interior of reservoir 45. The upper end of opening 64 is covered by the septum 48 which is in the form of a relatively thick rubber disk whose diameter is somewhat larger than that of opening 64. Septum 48 is held in place on plate 62 by a collar 66 having a reduced diameter upper end which forms the inlet port 46. Collar 66 is anchored to plate 62 by suitable means such as a weld. The segment of opening 64 between septum 48 and the lower or inner end of the opening constitutes a refill chamber 68 and a perforate needle stop 70 is usually present at the lower end of that opening to limit the extent to which a needle can be inserted into body 40.

A relatively large diameter recess 72 is formed at the underside of plate 62 within reservoir 45. Recess 72 communicates with a conduit 74 extending through plate 62 and projecting from the upper surface thereof where it connects to the inlet end of a long capillary tube 76 which is coiled around collar 66 at the upper surface of plate 62. The entrance into recess 72 is covered by a filter assembly shown generally at 78 mounted at the underside of plate 62. This filter assembly and the capillary tube 76 are described in greater detail in U.S. Pat. No. 4,978,338.

The outlet end of capillary tube 76 is connected to a conduit 78 which extends down through plate 62 on the opposite side of opening 64 therein from conduit 74. The lower end of conduit 78 leads to a recess 82 in the underside of plate 62 whose mouth is covered by a cover 84. Also extending through plate 62 adjacent to conduit 78 is a relatively large diameter passage 86 which conducts fluid from recess 82 to another recess 88 at the upper side of plate 62 and whose entrance is closed by a cover 92 mounted to the upper side of the plate.

Extending down into plate 62 from recess 88 is a blind hole 94. This hole intercepts a second blind hole 96 which extends in from the edge of plate 62 along a chord thereof; see FIG. 2. The proximate end of the outlet catheter 56 is connected to plate 62 so that it is in fluid communication with that hole 96.

Another blind hole 98 extends radially inward from the edge of plate 62 perpendicular to hole 96 so as to intercept hole 96. Hole 98 is countersunk at 98a to receive a connector 102 projecting out from the side of the bolus head 42.

As shown in FIG. 3, the pump's body 40 also includes an upper annular cover 104 which covers the upper surface of plate 62 and the components thereon, the central opening in the cover accommodating collar 66. The cover may be held in place by a suitable means such as welds between the edges of the cover and plate 62 and collar 66.

The pump also includes a lower cup-like cover 106 which covers reservoir 45 and whose edge is secured to the edge of plate 62 by welding or the like. The space 107 between reservoir 45 and the lower cover 106 may be filled with a suitable fluid such as triclorofluoromethane which vaporizes at physiological temperatures as described in the above patent. Thus body 10 functions as a vapor pressure pump whose reservoir 45 can be refilled and recharged simultaneously by inserting a hollow needle through the septum 48 and injecting additional infusate via refill chamber 68 into reservoir 45. Over time, that infusate will be pumped from the reservoir through filter assembly 78 to recess 72 and then through the capillary tube 76 which controls fluid flow. The fluid from the capillary tube then passes via conduit 78, recess 82, recess 88 to holes 94 and 96 and thence to the outlet catheter 56. Of course, other types of flow restrictors may be used in lieu of capillary tube 76. Also, known flow control electronics and a power supply may be included in body 40 under top cover 104.

Still referring to FIG. 3, the bolus head 42 is basically a generally cylindrical sub-assembly attached to the side of body 40. The head comprises a bottom section 122, a mid section 124 and a top section or cap 126 which are stacked one on top of the other. Bottom section 122 is a disk-like member having a relatively large central recess 132 which extends from the top of the section almost to the bottom thereof. Positioned slightly to the left of recess 132, i.e., toward main body 40, is a second small diameter vertical recess 134 in which is seated a coil spring 136. Recess 134 is countersunk so as to form an annular platform 134a with spring 136 projecting above the platform.

A retainer pin 138 projects up from platform 134a just to the left of spring 136. Pin 138 is arranged to retain one end of a lever 140 which extends from pin 138 into the large recess 132 in bottom section 122. The illustrated lever 140 is shaped more or less like a frying pan in that it has a circular cup-shaped section 140a in recess 132 and an arm or handle 140b which extends from section 140a over spring 136 to the retainer pin 138. Pin 138 is received in a hole 142 in the end of lever arm 140b which hole is somewhat larger than the pin 138 so that the lever 140 is free to swing up and down about the pin.

Also formed in the arm 140b of lever 140 for reasons that will become apparent is a lengthwise slot 144 which extends from hole 142 almost to the lever section 140a.

The midsection 124 of the bolus head 42 has the form of a circular plate with a central vertical passage 148 which has more or less the same diameter as the recess 132 in bottom section 122. However, the lower end of passage 148 has a reduced diameter to form an inside flange or shoulder 150 for supporting an interior self-sealing septum 152 in the form of a rubber disk. Preferably, a very coarse screen member 154 is situated underneath septum 152 to prevent downward deflections of septum 152. For example, the screen member 124 may consist of a plurality of spaced-apart, parallel, small diameter (0.020 in.) wires whose opposite ends are connected to a support ring seated on flange 150.

Figure 4:
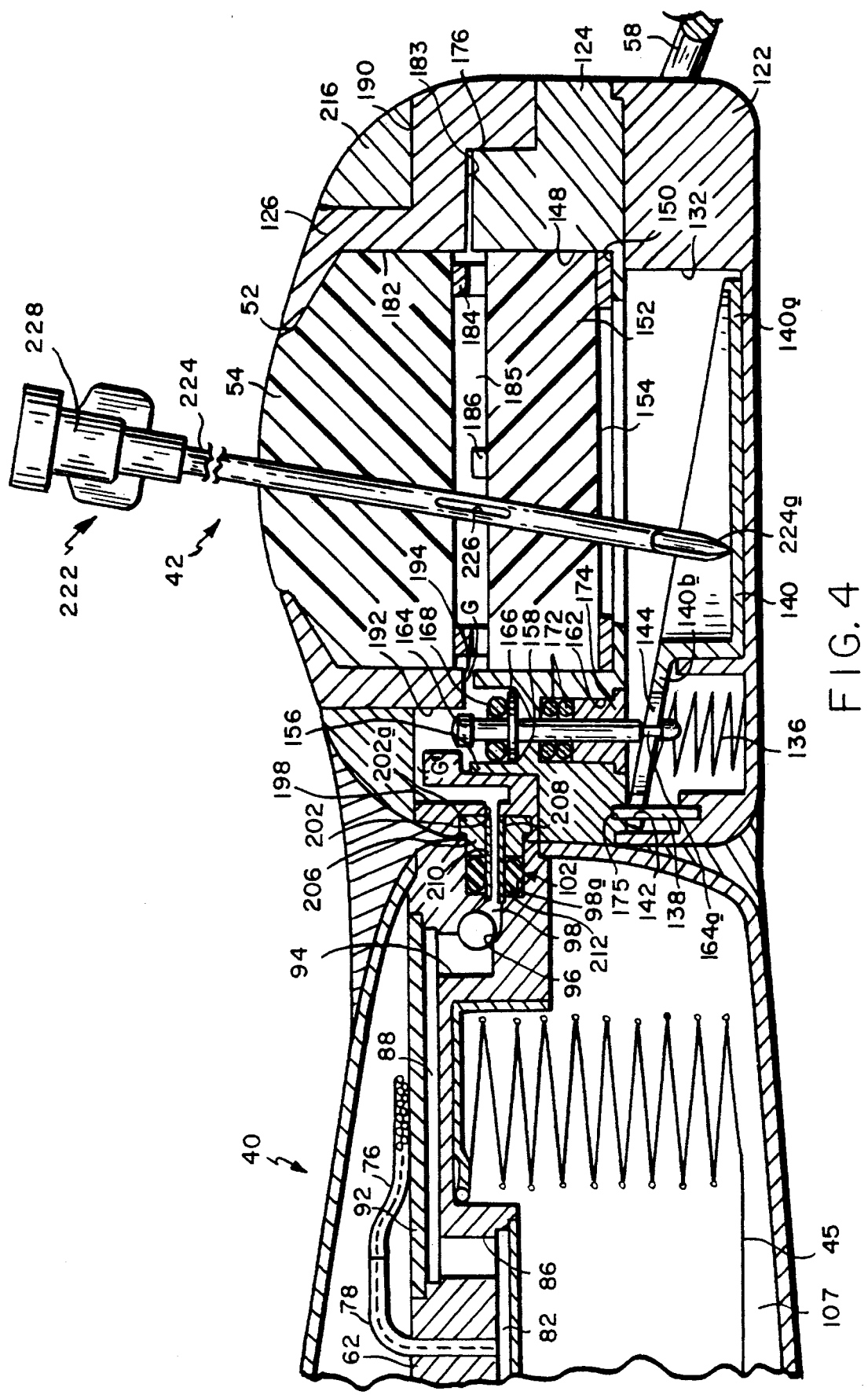
FIG. 4 is a similar view on a still larger scale showing the pump's safety valve in its open position.

Referring to FIG. 4, a vertical passage 156 extends down from the upper surface of midsection 124 just to the left of the passage 148 therein. That recess 156 is connected by a small diameter passage 158 to a vertical recess 162 in the underside of midsection 124 directly under passage 156. Slidably positioned in recesses 156, 162 and in passage 158 is a valve spool 164. The spool has a flange 166 formed adjacent to its upper end for supporting an 0-ring 168 which encircles the valve spool, the flange and O-ring being situated in passage 156. A pair of O-rings 172 also encircle the valve spool 164 within recess 162. These O-rings are held in place by a bushing 174 which closes the entrance to recess 162 and is secured to the underside of midsection 124. The O-rings 172 provide a sliding seal for the valve spool 164.

The lower end segment of valve spool 164 extends downward into the head bottom section 122, i.e., below the lever arm 140b therein. Also, the valve spool has a reduced diameter segment 164a adjacent to the lower end of the spool which is arranged to be slidably received in the slot 144 in the lever arm 140b. The valve spool 164 may be engaged in slot 144 by inserting the lower end of the valve spool down through the hole 142 in the lever arm and sliding it into the contiguous slot 144 prior to attaching the lever arm to the locating pin 138 in bottom section 122.

Once the valve spool 164 is attached to the lever 140, mid section 124 may be seated on bottom section 122 as shown in FIGS. 3 and 4. When so seated, the locating pin 138 engages in a hole 175 in the underside of midsection 124 just to the left of recess 162 therein. Such engagement establishes the proper angular alignment of the two head sections and captures the lever 140 on pin 138.

The upper surface of the bolus head midsection 124 is stepped at 176 for locating and seating the head's top section 126. Section 126 includes a large central opening 182, the upper end of which has a reduced diameter and forms the inlet port 52 of the bolus head 42. The bolus septum 54 is contained within that opening. The undersurface of top section 126 is stepped at 183 to conform to the step 176 in the upper surface of midsection 124 so that section 126 may seat tightly on section 124. However, prior to such seating, a flat spacer ring 184 is positioned on top of septum 152 in midsection 124 to maintain a space 185 between that septum and the septum 54 in top section 126. That space 185 constitutes a bolus chamber in head 42. Preferably, a plurality of notches 186 are provided in the underside of spacer ring 184 to allow for the flow of fluid from the bolus chamber 185 to the outside of the ring for reasons that will become apparent.

A circumferential notch 190 is provided in the upper surface of top section 126 radially outboard of opening 182 therein. Also, a small diameter vertical passage 192 is provided in top section 126 at notch 190 just to the left of the opening 182. Passage 192 is arranged and adapted to slidably receive the upper end of the valve spool 164 when the head's top section 126 is seated on midsection 124. Also, the under-surface area 194 of top section 126 around passage 192 is recessed slightly so that a narrow, e.g., 0.007 in., gap G exists between the upper surface of section 124 and the undersurface area 194. This gap G allows fluid to flow from the bolus chamber 185 between septa 54 and 152 through the spacer ring notches 186 to the recess 156 containing the valve spool 164. However, the narrow gap G prevents particulate matter from passing and possibly interfering with the proper operation of valve 164, 168.

A vertical blind hole 198 is provided at the notch 190 of top-section 126 just to the left of the passage 192 therein. This hole intercepts another short radial hole 202 extending in from the side of section 126. Hole 202 is countersunk at 202a to accept the connector 102 referred to above.

The connector 102 includes a bushing 206 whose central opening 208 is aligned with hole 202 and contains a tiny tube 210 which projects from the shank end of the bushing and carries an O-ring 212.

When bolus head 42 is coupled to main body 40, the shank end of bushing 206 and O-ring 212 seat in the countersunk hole 98a in the side of the main body plate 62 so that fluid communication is established between tube 210 and the holes 96 and 98 in plate 62. The O-ring 212 provides a fluid-tight seal between tube 210 and the plate 62.

The final component of head 42 is a ring 216 which seats in the notch 190 at the upper surface of top section 126. This ring covers the open upper ends of the passage 192 and hole 198 in section 126. It should be noted from FIG. 4, however, that the upper surface of section 126 is relieved in the area between passage 192 and hole 198 to provide a gap G between those openings so that fluid can flow between those openings.

The various sections of head 42 may be secured together by appropriate means such as welds. Likewise, head 42 may be secured to the side of main body 40 by welds which may then be covered by silicone elastomer or the like to form the contoured neck 44.

The pump's bolus head 42 normally reposes in the condition shown in FIG. 3. That is, the lever 140 is normally biased to its illustrated upper position by the spring 136. When the lever is in that position, the valve spool 164 is raised so that the O-ring 168 on the valve spool is pressed against the undersurface area 194 of top section 126 around the valve spool thus blocking the fluid path between the recess 156 in head midsection 124 and the passage 192 in section 126. Thus spool 164 and O-ring 168 constitute a safety valve.

On the other hand, when the lever 140 is moved to its lower position shown in FIG. 4 in opposition to the bias of spring 136, the valve spool is shifted downward thereby moving the O-ring 168 away from the undersurface area 194 of section 126. This allows fluid to flow from the bolus chamber 185 in head 42 through gap G into recess 156 whence the fluid may flow around the valve spool 164 into passage 192 in section 126 and through gap G into holes 198 and 202 in section 126. Furthermore, it may flow through connector 102 into the hole 98 in main body 40 and thence along hole 96 into the outlet catheter 56.

In use, the pump is implanted at a suitable location in a patient's body, e.g., in a subcutaneous pocket either below the clavicle or on the abdomen. It may be anchored there by suturing the rings 58 to adjacent tissue such that the pumps septa 48 and 54 lie directly under the skin. The outlet catheter 56 may be routed to a suitable location in the patient's vasculature e.g., the superior vena cava, heputic artery or intraspinal space. After implantation, the pump's reservoir 45 may be filled with infusate in the usual way by inserting a hypodermic needle with an open end through the septum 48 and injecting the desired drug, e.g., insulin, heparin, morphine, chemotherapy, etc., into the refill chamber 68 whence the liquid will flow into and fill the reservoir 45. The refilling of the reservoir also automatically recharges the vapor pressure pumping means in the space 107. As is known from the prior art, the liquid in the reservoir 45 will be pumped at a desired rate, e.g., 1 ml/day for insulin, through the outlet catheter 56 to the selected infusion site in the patient.

As noted above, normally the valve spool 164 is in its raised position so that the infusate from the reservoir 45 tends to flow through the hole 96 to the outlet catheter 56 rather than to the smaller and more restrictive hole 98 and connector 102 to the bolus head 42. Moreover, even if the infusate should follow that path, it would be unable to pass the O-ring 198 because 15 as noted above, the valve spool 164 is normally in its raised position pressing that O-ring against the undersurface area 194 of section 126.

When it is desired to administer a bolus of the same drug or another drug to the patient, this may be accomplished by inserting a special hypodermic needle shown generally at 222 in FIG. 4 through the stacked septa 54 and 152 of the bolus head 42. The needle 222 has a shaft 224 which is hollow, but unlike conventional needles, its pointed tip 224a is closed. Rather, an opening 226, is provided in the side of the needle shaft at a location thereon which is spaced from the tip 224a. More specifically, the side opening 226 in the shaft is positioned from the needle tip a distance more or less equal to the distance between the floor of recess 132 and the bolus chamber 185 in the bolus head 42 (less the thickness of the lever section 140a).

A standard Luer connector 228 is mounted to the upper end of the needle shaft 224 for connecting the needle to a standard syringe or other infusate source.

To administer a bolus to the patient, the needle 222 is inserted through the septa 54 and 152 so that the needle tip 224a contacts and moves the lever 140 to its lower position shown in FIG. 4. This lowers the valve spool 164 thereby establishing a fluid path between the bolus chamber 185 and the outlet catheter 56, bypassing the flow restrictor in the pump's main body 40. This positioning of the needle 222 also aligns the needle side opening 226 with the bolus chamber 185 so that a drug injected under pressure into the needle shaft 224 will flow out through the side opening 226 into the bolus chamber 185 and thence to the outlet catheter 56. Preferably, the side opening 226 is formed as a longitudinal slot to allow some tolerance in the angular placement of the needle 222 in the head 42.

It should also be noted that the stacked septa 54 and 152 hold the needle 222 with sufficient retentive force that the needle cannot be pushed out by the upward force of the valve spring 136 acting on the needle through the lever 140. This being the case, needle 222 may be left in place for an extended period so that supplemental continuous infusions may be administered through head 42 and the outlet catheter 56 of the implanted pump via an external drug administration system (not shown) connected to the hub 228 of needle 222.

Still further, as noted above, the screen 154 in head 42 prevents downward deflection of the lower septum 152 due to the fluid pressure developed in the bolus chamber 185. Yet, the screen is sufficiently coarse that it does not impede the passage of the needle 222 into the recess 132 in lower section 122.

As noted above, only a needle such as needle 222 with the proper side opening can be used to administer a bolus dose of infusate through our pump. If a standard hypodermic needle with an open tip such as is used to refill the pump's reservoir 45 should be inserted into the bolus head 42, it would not be able to deliver infusate to the outlet catheter 56. This is because such a needle could not possibly deliver infusate to the bolus chamber 185 while simultaneously depressing the lever 140 so as to open the safety valve 164, 168. In other words, if an ordinary needle with an open tip should be inserted through the septa 54 and 152 and depress lever 140, although the safety valve 164, 168 would be open, the recess 132 in which the needle tip is located is not connected to the bolus fluid pathway to outlet catheter 56 due to the presence of the O-rings 172 and bushing 174. Rather, the recess 132 constitutes a blind chamber. Preferably, that recess 132 is filled with an incompressable liquid such as distilled water at the time of the pump's manufacture so that no additional liquid can be introduced into that recess through an ordinary needle of the type used to refill the pump's reservoir 45.

If one should attempt to insert an ordinary needle only through the septum 54 so that the open tip of the needle is located in the bolus chamber 185, the infusate could not flow from that chamber to the outlet catheter 56 because the safety valve 164, 168 would be closed since that needle has not depressed the lever 140. Obviously also, if the tip of an ordinary needle lies in the material of either septum 54 and 152, no injection of fluid is possible because the rubber material of the septa would seal the open end of needle.

As an ordinary needle cannot be used to administer a bolus to the patient via head 42, so also the special bolus needle 222 cannot be used to refill the reservoir 45 in the pump's main body 40. More particularly, if the needle 222 should be inserted through the pump's refill septum 48, the needle side opening 226 would be located in the material of septum 48 so that no injection of infusate through that needle into the refill chamber 68 would be possible because the rubber material of septum 48 would seal that side opening.

It is apparent from the foregoing, then, that our pump positively prevents a healthcare professional from injecting a drug intended to refill reservoir 45 directly into the patient via the bolus head 42. Similarly, a bolus dose intended to be injected into the patient using the special needle 222 cannot be used to refill reservoir 45. Therefore, the pump positively prevents misdelivery of the drugs.

As seen from the foregoing description, both the main body 40 and bolus head 42 sections of the pump are composed of components which may be machined using standard techniques and may be assembled relatively easily without any special equipment. Therefore, the pump should be relatively easy and inexpensive to manufacture and assemble.

It will thus be seen that the objects set forth above, among those made apparent from the preceding description, are efficiently attained. Also, certain changes may be made in the above construction without the departing from the scope of the invention. For example, the pumpable infusate reservoir may be substituted for by a standard bolus chamber. In that event, the invention would prevent misdelivery of infusate into the two bolus chambers. Therefore, it is intended that all matter contained in the above description or shown in the accompanying drawings shall be interpreted as illustrative and not in a limited sense.

It is also to be understood that the following claims are intended to cover all of the generic and specific features of the invention described herein.

What is claimed is:

1. An implantable infusion device comprising a housing having a wall;

a first infusate chamber in the housing;

a first inlet port in said wall, said first inlet port communicating with said first chamber;

a first self-sealing septum closing said first inlet port at said wall;

an outlet catheter extending from said housing;

a first fluid pathway extending from said first chamber to said outlet catheter;

a second inlet port in said wall, said second inlet port extending into the interior of said housing;

a second self-sealing septum closing said second inlet port at said wall;

a third self-sealing septum positioned in the second inlet port and spaced from said second septum therein so as to define between said second and third septa a second infusate chamber in the housing;

a second fluid pathway extending from the second chamber to said outlet catheter;

a valve in said second fluid pathway, said valve being movable between open and closed positions to open and close the second fluid pathway;

means for biasing the valve to its closed position, and valve actuating means located in the second inlet port on the opposite side of the third septum from the second chamber, said actuating means being adapted to open said valve only when contacted by a needle that penetrates through both the second and third septa.

2. The device defined in claim 1 wherein a segment of the second inlet port extends away from said wall beyond the third septum to form a closed chamber within the housing;

said valve has a portion which extends into said closed chamber, and the valve actuating means comprise a lever pivotally mounted in said closed chamber and connected to said valve portion.

3. The device defined in claim 2 and further including means positioned in the housing between the third septum and the closed chamber for preventing the third septum from deflecting into the closed chamber.

4. The device defined in claim 2 wherein the closed chamber is filled with an incompressible liquid.

5. An implantable infusion device comprising a housing having opposite first and second walls;

a relatively large blind passage extending into the housing from the first wall toward the second wall;

a first self-sealing septum blocking the passage at the first wall;

a second self-sealing septum blocking the passage at a location therein spaced from the first septum thereby defining an infusate chamber between the first and second septa and a blind chamber between the second septum and the housing second wall;

a fluid pathway extending from the infusate chamber to the exterior of the housing;

a valve in said fluid pathway, said valve being movable between open and closed positions to open and close the fluid pathway;

a lever having a portion connected to said valve and being pivotally mounted in said blind chamber so that the lever is movable in said blind chamber between a raised position relatively close to the second septum wherein the valve is closed and a depressed position relatively close to the housing second wall wherein said valve is open, and means for biasing the lever to its raised position wherein said valve remains closed unless said lever is depressed by a needle penetrating said blind chamber.

6. The device defined in claim 5 wherein said blind chamber is filled with an incompressible liquid.

7. The device defined in claim 5 wherein said biasing means comprise a coil spring compressed between said lever and the housing second wall.

8. The device defined in claim 5 and further including a hollow needle having a closed pointed tip and a side opening spaced from said tip a distance approximately equal to the distance between said infusate chamber and the housing second wall so that when said needle is inserted through the first and second septa into said blind chamber sufficient to move the lever to its depressed position, the needle side opening is aligned with the infusate chamber.

9. The device defined in claim 8 wherein said needle side opening is elongated.

10. The device according to claim 5 and further including an infusate reservoir in the housing;

an inlet port extending from the housing first wall to said reservoir;

an additional self-sealing septum blocking the inlet port at said first wall, and a fluid conduit extending from said reservoir to said fluid pathway downstream from said valve.

11. The device defined in claim 10 wherein said infusate reservoir is a pumpable reservoir.

12. The device defined in claim 10 and further including a flexible outlet catheter having one end connected to said housing and being in fluid communication with said fluid pathway.

* * * * *